(12) United States Patent
Carrillo

(10) Patent No.: US 6,809,810 B2
(45) Date of Patent: Oct. 26, 2004

(54) DETECTION CELL

(75) Inventor: Albert L. Carrillo, Redwood City, CA (US)

(73) Assignee: Applera Corporation, Foster City, CA (US)

( * ) Notice: Subject to any disclaimer, the term of this patent is extended or adjusted under 35 U.S.C. 154(b) by 126 days.

(21) Appl. No.: 09/972,009

(22) Filed: Oct. 4, 2001

(65) Prior Publication Data

US 2003/0067599 A1 Apr. 10, 2003

(51) Int. Cl.⁷ ............................................. G01N 1/10
(52) U.S. Cl. ..................... 356/246; 356/344; 356/440; 422/104
(58) Field of Search ............................... 356/244, 246, 356/344, 440; 204/603; 422/82.05, 82.08, 82.09, 101, 104

(56) References Cited

U.S. PATENT DOCUMENTS

| | | | | |
|---|---|---|---|---|
| 3,556,659 A | * | 1/1971 | Hawes | ........................ 356/301 |
| 3,583,817 A | * | 6/1971 | Rachlis et al. | .............. 356/410 |
| 4,534,651 A | * | 8/1985 | Minikane | ..................... 356/440 |
| 4,657,870 A | * | 4/1987 | Ryder et al. | .............. 435/287.4 |
| 5,324,401 A | | 6/1994 | Yeung et al. | |
| 5,529,679 A | * | 6/1996 | Takahashi et al. | ........... 204/603 |
| 5,599,503 A | | 2/1997 | Manz et al. | .............. 422/82.05 |
| 6,143,248 A | | 11/2000 | Kellogg et al. | ................ 422/72 |
| 6,188,813 B1 | | 2/2001 | Dourdeville et al. | |
| 6,490,034 B1 | * | 12/2002 | Woias et al. | ................. 356/246 |

OTHER PUBLICATIONS

International Search Report from PCT/US02/31385 mailed Mar. 19, 2003.

* cited by examiner

Primary Examiner—Hoa Q. Pham

(57) ABSTRACT

The detection cell includes a substrate that defines a cavity. The cavity has a substantially planar floor and at least one wall with an opening there through. The detection cell also includes a prism disposed adjacent the opening. The prism is configured to redirect light through the opening into the cavity at an angle substantially parallel to the floor. Once a chemical sample is positioned in the cavity, light is directed at the prism. The prism is disposed adjacent an opening leading into a cavity containing a chemical sample. Subsequently the light is reflected within the prism to pass through the opening and into the cavity to illuminate the chemical sample.

21 Claims, 10 Drawing Sheets

DETECTION CELL

BACKGROUND OF THE INVENTION

1. Field of the Invention

The invention relates generally to photometrically analyzing a sample in a chemical detection system. More particularly, the invention is directed to an apparatus and method for uniformly illuminating a sample in a microchannel array or detection cell of an electrophoresis system using a prism arrangement.

2. Description of the Related Art

The separation and analysis of chemical samples is widely used in both chemistry and biotechnology. In order to increase the speed and efficiency at which chemical samples are evaluated, chemical samples are separated into their component parts and simultaneously analyzed.

One such separation technology, electrophoresis, is used in DNA sequencing, protein molecular weight determination, genetic mapping, and other types of processes used to gather large amounts of analytical information about particular chemical samples. Electrophoresis is the migration of charged colloidal particles or molecules through a solution under the influence of an applied electric field usually provided by immersed electrodes, where the colloidal particles are a suspension of finely divided particles in a continuous medium.

Historically, a polymer gel containing the finely divided particles was placed between two glass plates and an electric field applied to both ends of the plates. This method, however, offered a low level of automation together with long analysis times.

More recently, capillary electrophoresis (hereinafter "CE") was developed, which has the added advantages of speed, versatility and low running costs. Operation of a CE system involves application of a high voltage (typically 10–30 kV) across a narrow bore capillary (typically 25–100 $\mu$m). The capillary is filled with electrolyte solution which conducts current through the inside of the capillary. The ends of the capillary are dipped into reservoirs filled with the electrolyte. Electrodes made of an inert material such as platinum are also inserted into the electrolyte reservoirs to complete the electrical circuit. A small volume of sample is injected into one end of the capillary. Application of the voltage causes movement of sample ions towards their appropriate electrode. Different sample ions arrive at a detection part of the capillary at different times. The sample may be labeled with a fluorescent marker so that when the sample passes through a beam of light at the detector the fluorescent marker fluoresces and the fluorescence is detected by a detector, usually a UV detector, as an electric signal. The intensity of the electric signal depends on the amount of fluorescent marker present in the detection zone. The plot of detector response versus time is then generated, which is termed an electropherogram.

CE is a particularly preferred separation method, as it allows the use of high electric fields due to the capillary tube efficiently dissipating the resulting heat produced by the electric field. As such, the separations achieved are much better than the more traditional electrophoretic systems. In addition, multiple capillary tubes may be closely spaced together and used simultaneously to increase sample throughput.

In traditional CE systems, analysis or detection of the separated components is performed while the sample is still located within the capillary and may be accomplished using photometric techniques such as adsorbance and fluorescence. These photometric techniques direct excitation light toward the capillary tube. Light emitted from the sample (e.g., fluorescence) is then measured by a detector, thereby providing information about the separated components. Therefore, in these systems, excitation light directed at the sample, as well as light emitted from the sample, must be transmitted through the capillary's walls. A drawback of this approach is that the fused silica capillaries typically used in capillary electrophoresis are poor optical elements and cause significant scattering of light. The problem associated with light scattering is exacerbated by having multiple capillaries disposed side-by-side, as scattered excitation light from one capillary interferes with the detection of samples in neighboring capillaries.

One approach to solving the problem of on-capillary detection has been to detect a sample after the sample emerges from the capillary in a detection cell having superior optical characteristics, e.g., a flat quartz chamber. In this system, a sample is transported from the outlet of a capillary to the detection cell by electrophoresis under the influence of the same voltage difference used to conduct the electrophoretic separation. Examples of this type of system are disclosed in U.S. Pat. No. 5,529,679, which is incorporated herein by reference.

A variation of the above system replaces the capillary tubes with a series of parallel micro-channels formed in a plate or chip, where the micro-channels are in fluid communication with a detection cell in a manner similar to that described above. This CE layout is known as a micro-channel array.

While addressing some of the abovementioned problems, the detection cell type CE system has drawbacks of its own. For example, excitation energy, such as light from a laser, has the tendency to scatter, thereby diminishing the energy's intensity as it transmitted through the detection cell.

A partial cross-section of a prior art detection cell 102 is shown in FIG. 1A. The detection cell 102, typically made from glass substrate, forms a cavity 108, which is filled with an electrolytic polymer 110 containing a sample to be detected. The cavity 108 is then typically covered with a transparent cover 118. Excitation light 104, typically from a laser, enters the detection cell 102 at a first end 112. Because the first end 112 is normal to the excitation light 104, the light 104 does not scatter, i.e., reflect or refract, when passing into the detection cell, from air to glass. However, when the light 104 passes through the boundary 106 between the detection cell and the polymer 110, the light is refracted. This is due to the angle or slope of the boundary 106, and the difference in refractive indices of the glass and polymer. The angle or slope of the boundary 106 is caused by current etching and mastering technologies, which are typically unable to produce optically flat vertical cavity walls in glass or plastic cavities 108 of the required dimensions.

The refracted light obeys the law of refraction, i.e., $$RI_I \sin(A_I) = RI_R \sin(A_R)$$

where $RI_I$=first refractive index;

$A_I$=angle of incidence;

$RI_R$=second refractive index; and $A_R$=angle of refraction.

As the polymer has a refractive index (approximately 1.41) less than the refractive index of glass (approximately 1.52), the angle of refraction is larger than the angle of incidence and the light bends further away from the normal to the boundary 106. Much of the excitation light is lost due to light escaping 116 out of the detection cell instead of being trapped in the cavity by Fresnel reflection. This degrades the intensity of excitation light incident on the samples, which in turn adversely affects the strength of the detected signal. Furthermore, refracted light rays may also reflect 114 off the internal surfaces of the cavity 108 causing interference and, therefore, degradation of the detection signal. In other words, the curved or angled interfaces or boundaries in combination with the unfavorable refractive index change at the glass to polymer boundary or interface, leads to unsatisfactory light intensity and quality, and consequently poor sample detection.

Moreover, the first end 112 through which the light first passes must be optically flat so that the light is not distorted. This requires the first end 112 to be polished, which is both expensive and time consuming.

Also, the substrate through which the light passes before entering the cavity may contain defects, such as voids, contaminants, or non-homogeneous material that creates density gradients. These defects can cause the light to scatter, refract, reflect, or the like, all of which degrade the light quality and hence detected signal.

In light of the above, there is a need for a more efficient means for directing light into a cavity while addressing the abovementioned drawbacks.

BRIEF SUMMARY OF THE INVENTION

According to an embodiment there is provided a detection cell of an electrophoresis system. The detection cell includes a substrate that defines a cavity. The cavity may have a substantially planar floor and at least one wall with an opening there through. The detection cell also may include a prism disposed adjacent the opening. The prism is configured to redirect light through the opening into the cavity at an angle substantially parallel to the floor.

The prism may include a transparent exit surface disposed adjacent, and bounding, the opening and a reflector inclined at an acute angle to the transparent surface. The reflector is configured to redirect light substantially orthogonally through the transparent surface into the cavity. The prism may also include a transparent entry surface disposed substantially perpendicular to the exit surface.

In another embodiment, a shaft is bored at least partially through the substrate adjacent the opening. The shaft is inclined substantially perpendicular to the floor. The prism is then positioned within the shaft.

In an alternative embodiment, the prism includes an additional reflector disposed substantially parallel to the reflector. The additional reflector is configured to redirect light from a light source at the reflector.

Further, according to various embodiments there is provided an additional prism disposed adjacent an orifice in an additional wall of the cavity opposing the opening. The additional prism is configured to redirect light exiting through the orifice away from the cavity to avoid light scatter. The additional prism may include a transparent exit surface disposed adjacent the orifice and a reflector inclined at an acute angle to the transparent exit surface. The reflector is configured to redirect light away from the cavity at an angle substantially perpendicular to the floor.

Still further, according to various embodiments there is provided a method for illuminating a chemical sample. A chemical sample is positioned in the cavity. Light is firstly directed at a prism. The prism is disposed adjacent an opening leading into a cavity containing a chemical sample. Subsequently the light is reflected within the prism to pass through the opening and into the cavity to illuminate the chemical sample.

Various embodiments address the above described drawbacks by guiding light into a detection cell using a light guide, such as a prism. The light guide provides a controlled reflector near the entry of a cavity. The reflector of the light guide is isolated from the chemistry in the cavity by a transparent surface that may form part of the light guide itself. In an alternate embodiment an additional reflector of the light guide redirects light to the reflector of the light guide so that the light may be directed into the detection cell from any chosen orientation. The transparent surface of the light guide forms part of the light guide's wall. The various surfaces of the light guide are made optically flat to eliminate beam reshaping and refraction issues. Also, since the transparent surface is flat, the unfavorable index of the polymer does not affect the light beam entry into the cavity.

Furthermore, cavity illumination overcomes the problems of not having a clean optical surface on the edge of the substrate by bringing the light in though a shaft somewhere within the edges of the substrate. The cross-section of the shaft can be either square, round, or other polygonally shaped form.

BRIEF DESCRIPTION OF THE DRAWINGS

For a better understanding of the nature and objects of the invention, reference should be made to the following detailed description, taken in conjunction with the accompanying drawings, in which.

Like reference numerals refer to corresponding parts throughout the several views of the drawings.

DETAILED DESCRIPTION OF THE INVENTION

For ease of explanation the following is described in use with a micro-channel plate. However, it should be appreciated that the described embodiments may be used with any chemical analysis device where control of light through a boundary between substances having different refractive indices is important, such as in a capillary electrophoresis device.

Figure 2A:
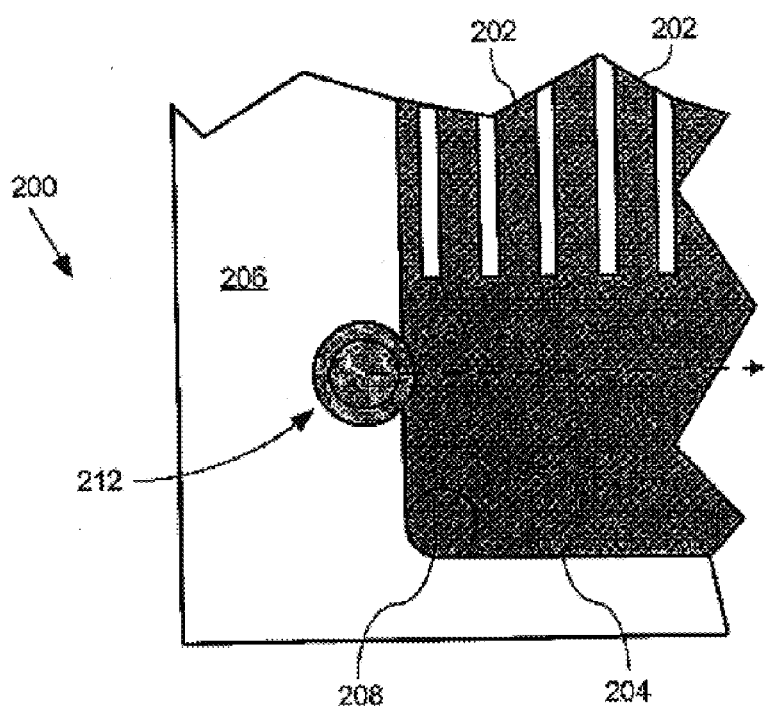
FIG. 2A is a partial top view of a detection cell according to an embodiment of the invention.
Figure 2B:
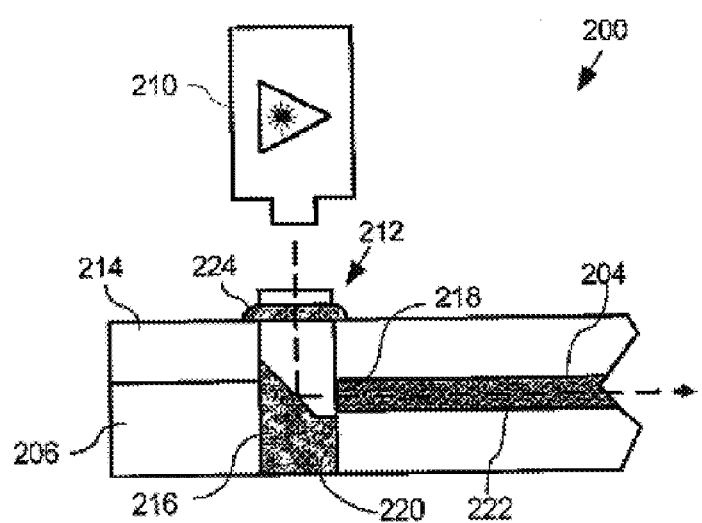
FIG. 2B is a partial side view of the detection cell shown in FIG. 2A.

FIG. 2A is a partial top view of a detection cell 200 according to an embodiment of the invention. The detection cell 200 may comprise a substrate 206 having a cavity 204 formed therein, as best seen in FIG. 2B. The substrate may be a transparent material such as glass or plastic. Some candidate materials are borosilicate glass (such as SCHOTT BOROFLOAT or 0211 CORNING glass), acrylic (such as polymethylmethacrylate (PMMA)), or ZEONOR/ZEONEX grade plastics.

The cavity 204 is a shallow hollow for receiving a chemical sample and has an opening 218 extending therefrom. The cavity 204 is filled with an electrolyte solution such as an electrolytic polymer. In one embodiment, the polymer is APPLIED BIOSYSTEMS POP-6 POLYMER GEL MATRIX. The detection cell 200 may also include an inlet 208 for filling the first cavity 204 with the electrolyte solution.

FIG. 2B is a partial side view of the detection cell 200 shown in FIG. 2A. A cover 214 cover the substrate 206. Because the cavity 204 had a shallow depth, light entering the cavity 204 should travels substantially parallel to the floor 222 of the cavity 204, so as not to scatter. A light guide 212 may be positioned adjacent the cavity 204. The light guide 212 is an optical instrument that contains reflecting elements, such as mirrors and prisms, to permit the displacement of light. To position the light guide 212 adjacent to the cavity 204, a shaft 220 is first bored through the cover 214 and substrate 206 so that part of the cavity 204 is in fluid communication with the shaft 220. The shaft may be square in cross-section as shown in FIGS. 4, 7, and 8, but alternatively may be any shape, such as rectangular or circular as shown in FIG. 2. In one embodiment, the shaft is 2 mm square in cross-section and is bored or drilled by ultrasonic drilling with an abrasive media or slurry. The abrasive media are either larger than the cavity (approximately 50 microns) to keep the abrasive media from entering the cavity or smaller than the cavity (approximately 8 to 20 microns) so that the abrasive media can be easily flushed out of the cavity. Alternatively, de-ionized and filtered water is pumped from an opposing side of the cavity with a pressure sufficient to keep the slurry from getting into the cavity.

The light guide 212 is then inserted into the shaft 220. The light guide is then bonded into place by an epoxy 216 and 224. Alternatively, the light guide can be fused to the plate (see FIGS. 2A, 2B, 4A, and 4C). Optionally, gaskets or seals could also be used to keep the fluid in the cavity from escaping. In this way, the surface of the light guide 212 bounding the cavity blocks the fluid communication between the cavity 204 and the shaft 220 or at least to block fluid from escaping the cavity.

Figure 3:
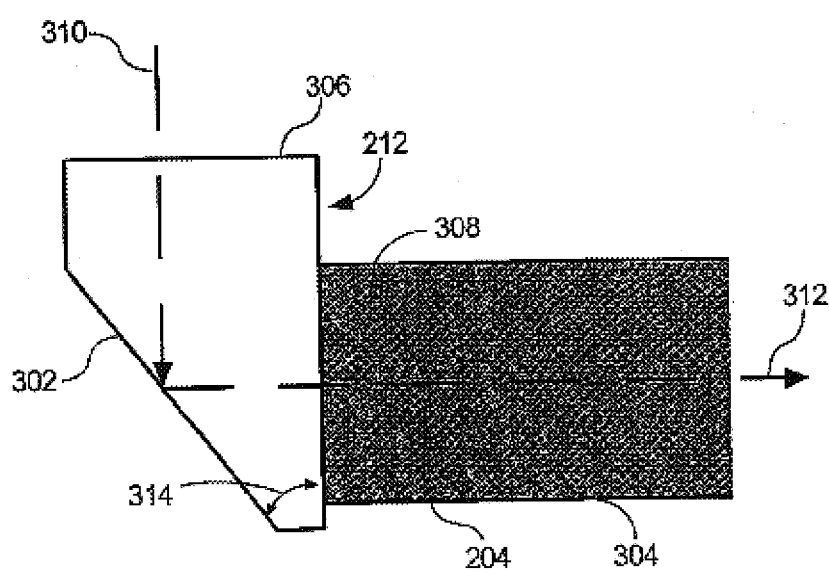
FIG. 3 is a close-up view of part of the detection cell shown in FIG. 2B.

FIG. 3 is a close-up view of the light guide 212 of the detection cell 200 shown in FIG. 2B. The cavity 204 is configured to receive a chemical sample contained within an electrolyte solution 304. The light guide also comprises a transparent surface 308 bounding at least part of the cavity 204 and a reflector 302 inclined at an acute angle 314 to the transparent surface 308. The reflector 308 is a reflective surface that is configured to redirect light 310 substantially orthogonally through the transparent surface 308 into the cavity 204. The light guide 212 may also include an additional transparent surface 306 that is inclined substantially perpendicular to the transparent surface 308. In one embodiment, the reflector 302, transparent surface 308 and additional transparent surface 306 form a prism. More specifically, the prism may be a right-angled prism with the reflector being the hypotenuse. The outer surface of the reflector may be silvered, coated, or metallized with a metallic substance to better reflect the incoming light beam 310. Also, the light guide 212 may be made of glass such as a BK-7.

The transparent surface 308 seals the open end of the cavity 204 so that the electrolyte solution 304 cannot flow out of the cavity into the shaft 220 (FIG. 2B). The incoming light beam 310 is directed into the light guide 212 and thereafter redirected as a reflected beam 312 that passes into the cavity orthogonally through the transparent surface 308. In this way, the light is not refracted when entering the cavity 204. Therefore, the entry of the reflected beam 312 into the cavity 204 can be accurately controlled and scatter reduced.

In an alternative embodiment, the additional transparent surface 306 maybe inclined relative to the transparent surface 308. The additional transparent surface 306 must, however, always remain substantially orthogonal to the incoming light 310. In this embodiment, the angle 314 would differ to that for the previous embodiment to ensure that the reflected beam 312 passes orthogonally through the transparent surface 308.

Figure 4A:
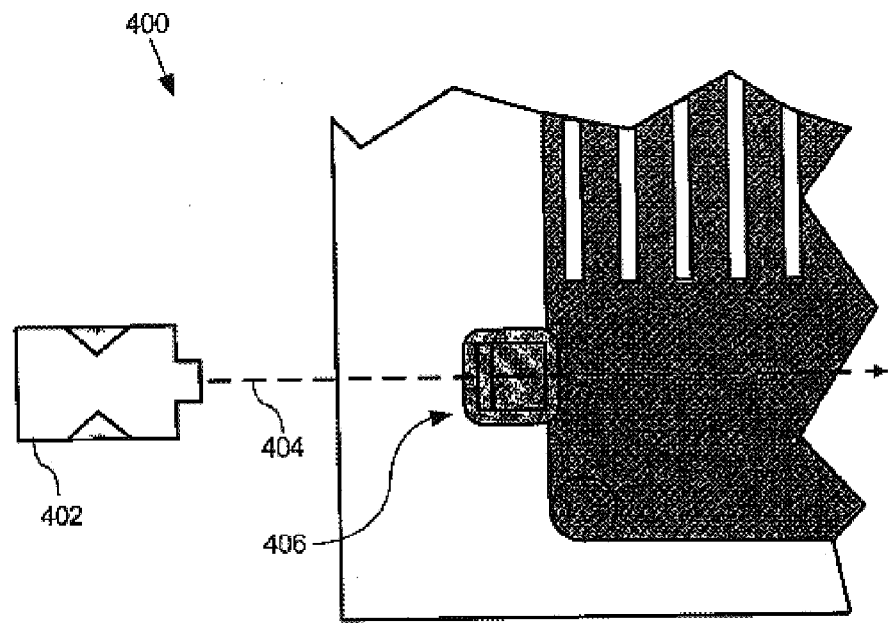
FIG. 4A is a partial top view of a detection cell according to another embodiment of the invention.
Figure 4B:
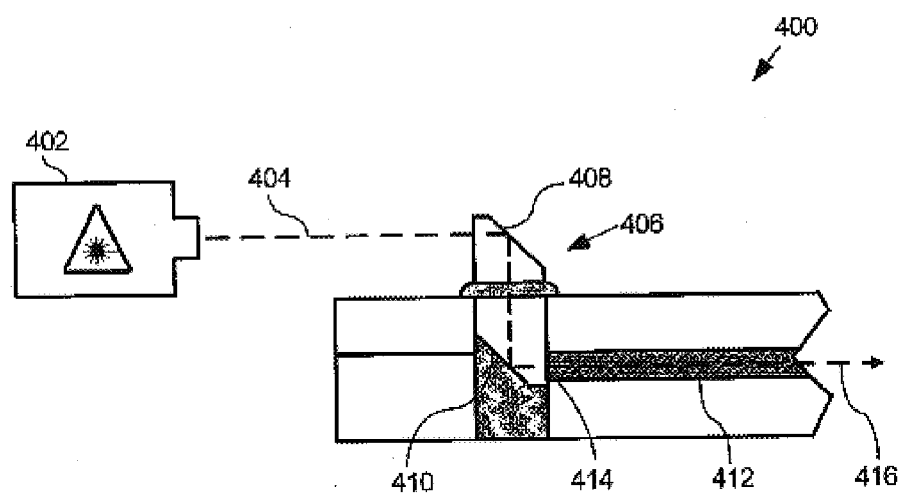
FIG. 4B is a partial side view of the detection cell shown in FIG. 4A.

FIG. 4A is a partial top view of a detection cell 400 according to another embodiment of the invention, and FIG. 4B is a partial side view of the detection cell 400 shown in FIG. 4A. In this embodiment a light source 402 projects a light beam 404 in a direction substantially parallel to the direction of the desired reflected beam within the cavity 412. To accomplish this, a light guide 406 is used. In this embodiment the light guide 406 includes a reflector 410 and an additional reflector 408. The additional reflector 408 redirects an incoming light beam 404 at the reflector 410. The reflector 410 then redirects a reflected light beam 416 into the cavity as described in relation to FIGS. 2A, 2B, and 3.

Figure 5A:
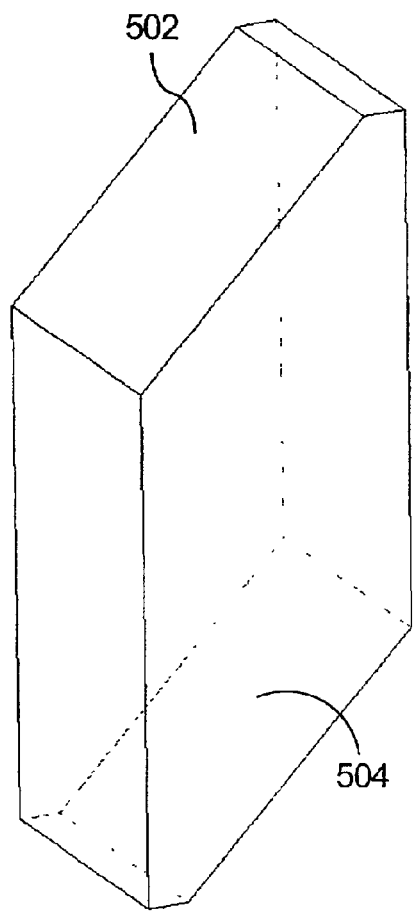
FIGS. 5A–5D are isometric three dimensional views of various prisms according to various different embodiments of the invention.
Figure 5B:
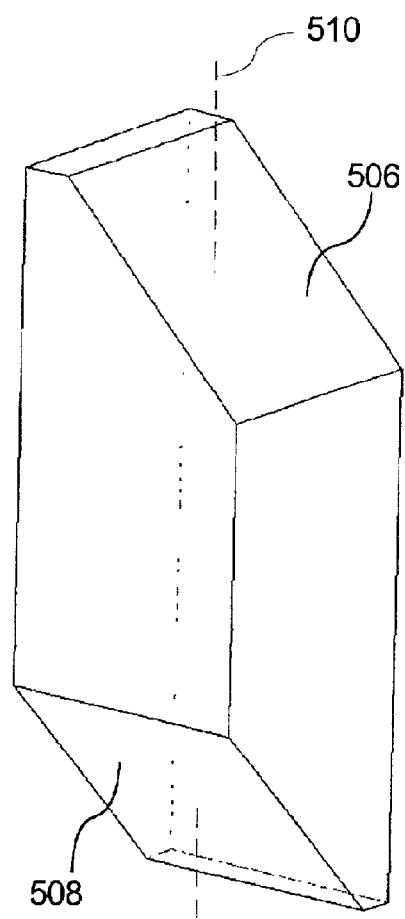

The light guide 406 comprises a rhomboidal prism similar to that shown in FIG. 5A. Alternatively, the light guide 406 may comprise two right-angled prisms similar to those shown in FIG. 5C. Still further, the reflectors 408 and 410 of the light guide 406 may alternatively comprise two parallel mirrors. In all of the aforementioned embodiments the light guide must include a transparent surface 414 through which the reflected light beam 416 orthogonally passes into the cavity 412. If the reflected light beam is not orthogonal to the transparent surface 414, the reflected light beam will refract and, thereby, adversely affect the quality of light in the cavity 412 and hence any detected signal. FIGS. 5A–5D are isometric three dimensional views of various prisms according to various different embodiments of the invention. FIG. 5A shows a rhomboidal prism with a first reflector 502 parallel to a second reflector 504. FIG. 5B shows a variation of the rhomboidal prism where a first reflector 506 has been rotated through ninety degrees about axis 510, in relation to the second reflector 508. This prism not only displaces an incoming light beam by the distance between the reflectors 506 and 508 but also rotates the beam through ninety degrees about axis 510.

Figure 5C:
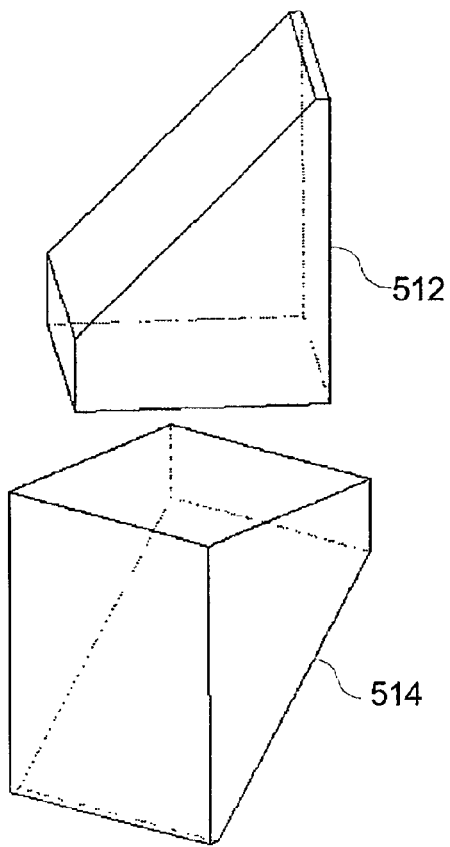
Figure 5D:
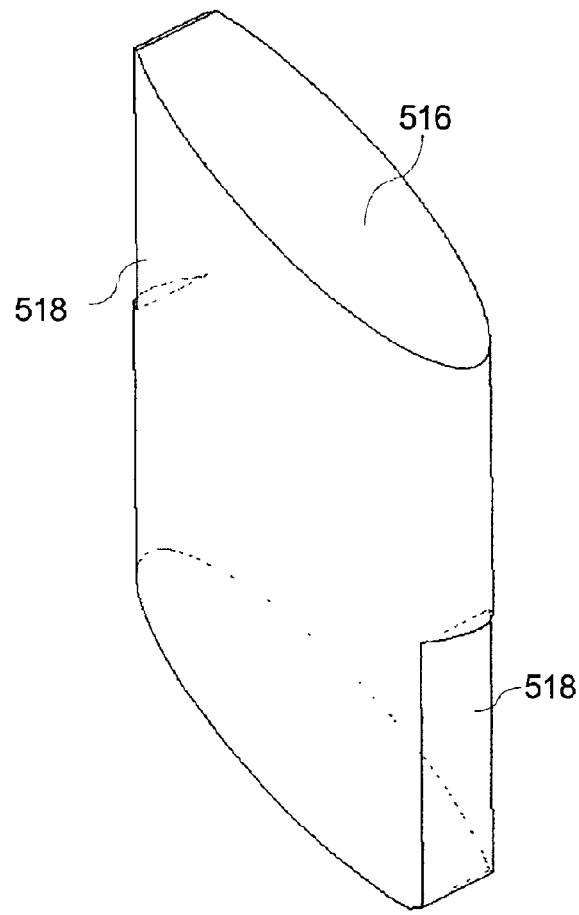

FIG. 5C shows two right-angled prisms 512 and 514. These prisms can be rotated relative to one another to adjust for light beam entry orientation as well as light beam exit orientation. FIG. 5D is a circular cylindrical prism 516. Notice that flat surfaces 518 are necessary at the light beam entry and exit surfaces to avoid beam shaping or distortion from the cylindrical wall shape. It should be appreciated that the light guide and/or prism can be any shape other than that described above, such as an elliptical cylindrical prism or the like.

Therefore, to summarize, the light guide's reflective surfaces may be angularly offset or linearly offset to allow the light to enter from any direction (see FIGS. 5B and 5C). If light enters vertically from above or below the detection cell, only the bottom half of the light guide is required (see FIGS. 2A and 2B). The light guide may be made from multiple and separate components (see FIG. 5C), but in its simplest form it is made of a single component. The light guide cross-sectional shape is square or cylindrical, but it is not limited to these shapes (see FIGS. 5A–5D). The light guide can be bonded into the detection cell with an adhesive (such as epoxy) or fused to the plate (see FIGS. 2A, 2B, 4A, and 4C). Alternatively, gaskets or seals could be used to keep the fluid in the cavity from escaping. The light guide's reflective surfaces may be mirrorized but could be any interface condition that causes light to totally internally reflect such as an optical coating or interface with a lower refractive index fluid.

Figure 6:
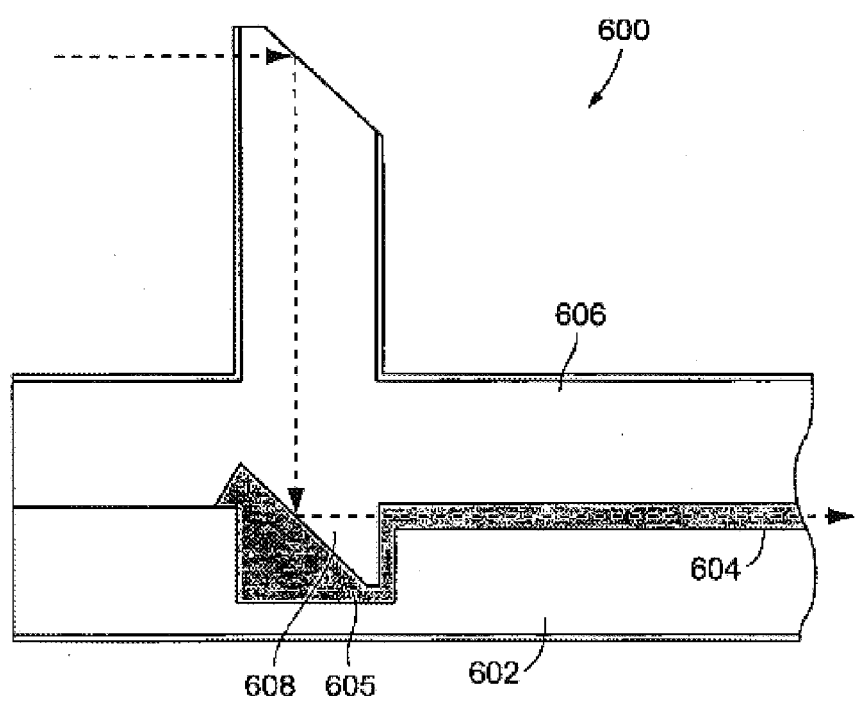
FIG. 6 is a partial side view of a detection cell according to yet another embodiment of the invention.

FIG. 6 is a partial side view of a detection cell 600 according to yet another embodiment of the invention. In this embodiment a substrate 602 defines both a cavity 604 having a substantially planar floor and an additional cavity 605. The cavity 604 has an opening therethrough leading into the additional cavity 605. In use, a cover 606 is placed directly onto the substrate 602. The cover 606 includes an integrally formed prism 608 for redirecting light into the cavity 604. It should however be appreciated that the prism 608 may be integrally formed with any part of the detection cell 600, so long as it causes light to be redirected into the cavity 604 substantially parallel to the floor of the cavity 604. The prism 608 is disposed adjacent the opening of cavity 604. The prism 608 is configured to redirect light through the opening of the cavity 604 into the cavity in a direction substantially parallel to the floor of cavity 604.

a prism disposed adjacent said opening, where said prism is configured to redirect light through said opening into said cavity in a direction substantially parallel to said floor.

Figure 1:
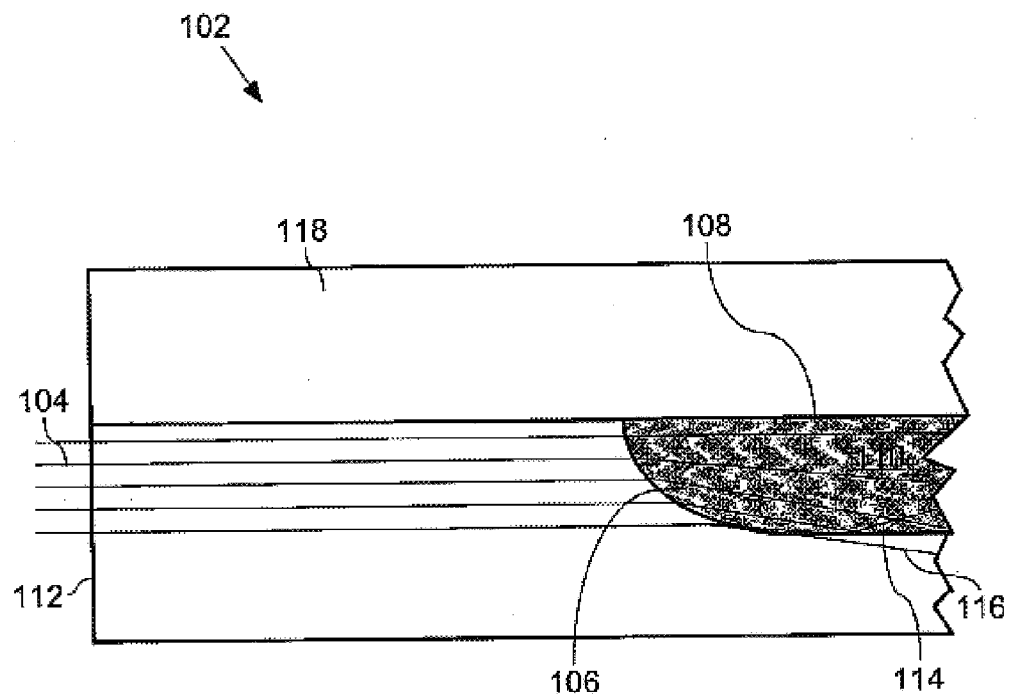
FIG. 1 is a partial cross-section of a prior art detection cell.
Figure 7A:
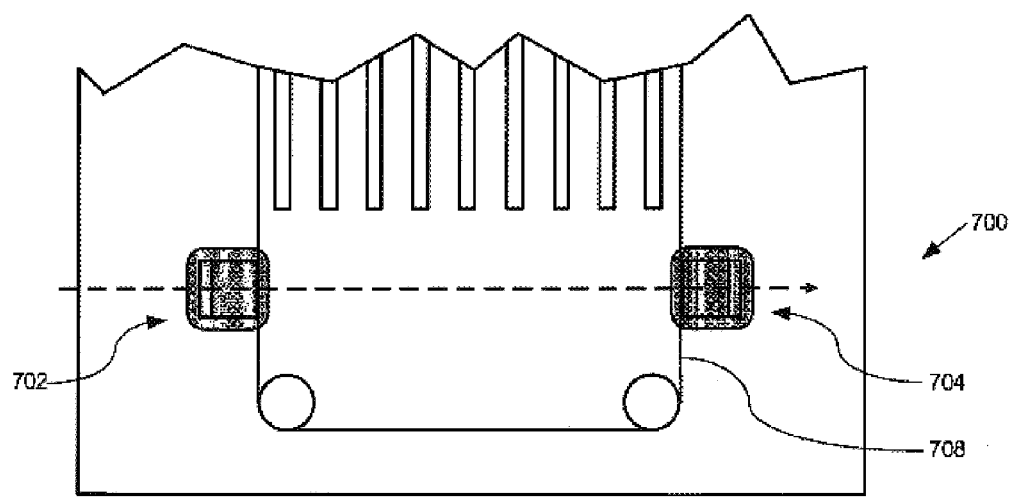
FIG. 7A is a partial top view of a detection cell according to yet another embodiment of the invention.
Figure 7B:
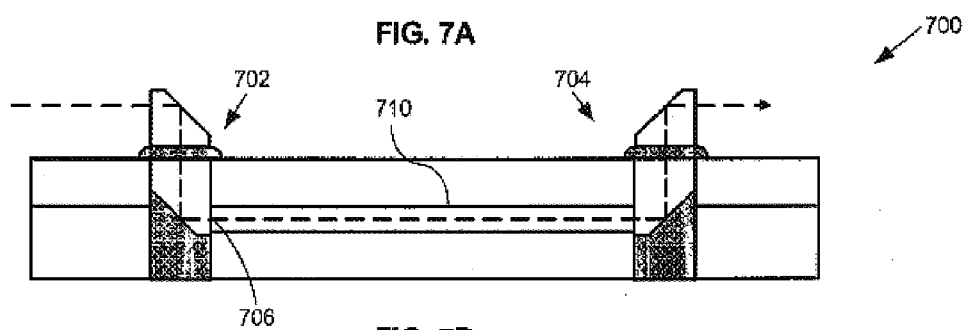
FIG. 7B is a partial side view of the detection cell shown in FIG. 7A.

FIG. 7A is a partial top view of a detection cell 700 according to yet another embodiment of the invention, and FIG. 7B is a partial side view of the detection cell 700 shown in FIG. 7A. As explained above in relation to FIG. 1, once a light beam has traversed a cavity 710 it would normally strike a wall 708 opposing a transparent surface 706 where the light beam enters the cavity 710. Due to manufacturing processes, as explained above, the wall 708 of the cavity has a curved or convex shape. This shape in combination with the different refractive indices of the electrolyte solution and the substrate refract the light at the wall 708 causing unwanted scattering of the light beam and possible reflections increasing background and stray light. To address this problem an additional light guide 704 can be positioned on the opposing side of the cavity from light guide 702. The light beam now has a outlet from the cavity and, therefore, does not scatter. The additional light guide 704 may be designed to direct the exiting light beam in any desired direction.

Figure 8A:
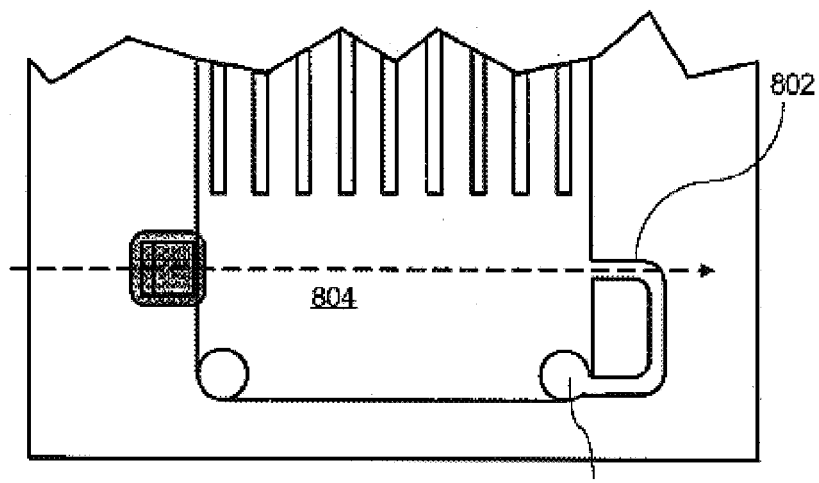
FIGS. 8A–8C are partial top views of detection cells according to various different embodiments of the invention.
Figure 8B:
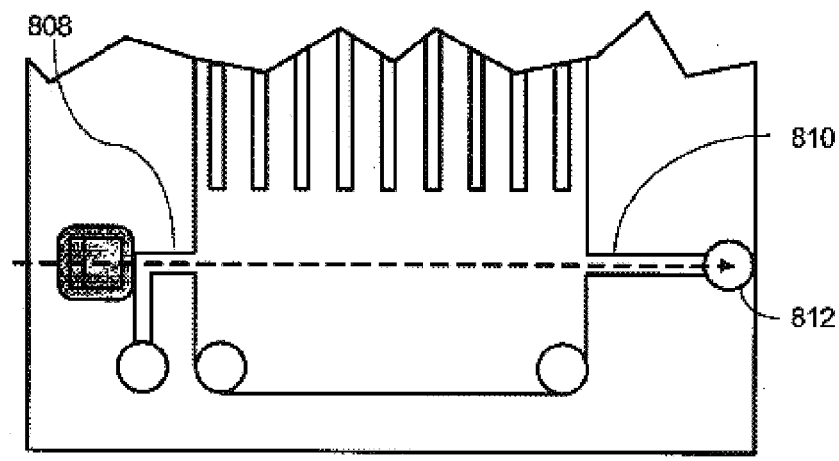
Figure 8C:
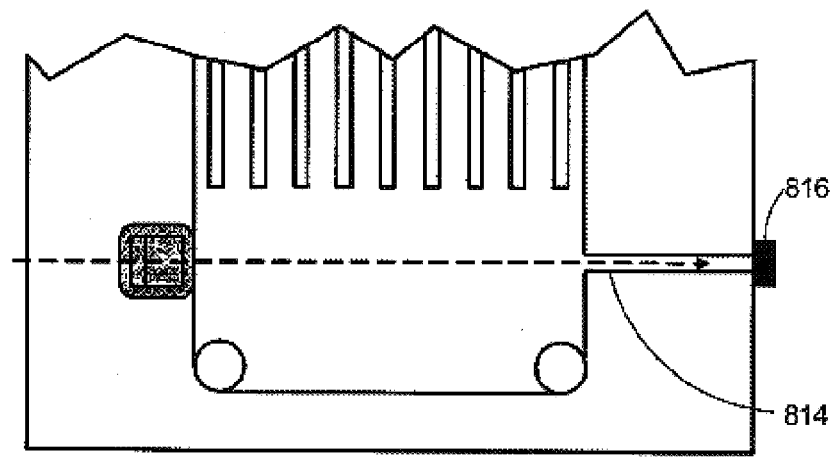

FIGS. 8A–8C are partial top view of detection cells according to various different embodiments of the invention. To alleviate the problems described in the description of FIG. 6 various other embodiments may be utilized. FIG. 8A shows a curved exit channel 802 through which the exiting light beam can pass. The exit channel is supplied with electrolyte solution from the cavity 804 and inlet 806. In this way, light scatter is diverted away from the cavity 804. FIG. 8B shows both an entry channel 808 and an exit channel 810 terminating in port 812. In this way, light scatter is avoided as the light passes into the port 812. FIG. 8C shows an exit channel 814 and a flat plate 816 bonded to the side of the exit channel 814. The flat plate is made from a material with a black opaque surface that acts as a beam stop. In this way, light scatter is avoided as the light is absorbed by the flat plate 816.

Figure 9:
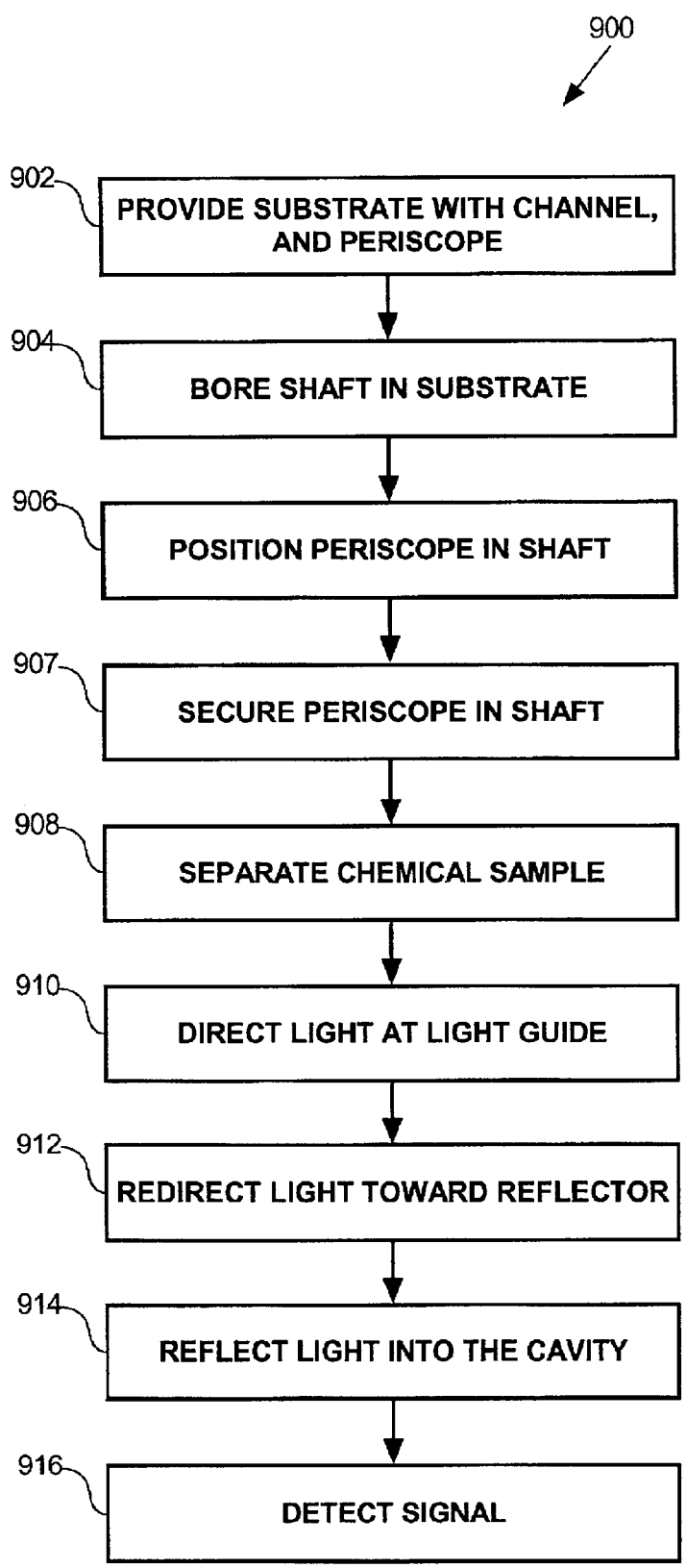
FIG. 9 is a flow chart of a method for illuminating a chemical sample according to an embodiment of the invention.

FIG. 9 is a flow chart of a method 900 for illuminating a chemical sample according to an embodiment of the invention. First, a substrate 206 (FIG. 2B) having a cavity 204 (FIG. 2B) and a light guide 212 (FIG. 2B) is provided 902. A shaft 220 (FIG. 2B) is then bored 904 through the substrate, as described above. The light guide is positioned 906 within the shaft and secured 907 in place by bonding the light guide into place or by fusing the light guide with the substrate.

The chemical sample is separated 908 as follows. A small volume of a chemical sample is injected into capillaries or micro-channels 202 (FIG. 2) and an electric field applied across the polymer, which causes movement of chemical sample ions through the polymer. Different chemical sample ions arrive at a detection cavity of the detection cell at different times. The chemical sample may be labeled with a fluorescent marker so that when the sample passes through a beam of light at the detector, the fluorescent marker fluoresces and the fluorescence is detected as an electric signal.

Light is then directed 910 at the light guide from a light source 210 (FIG. 2B), such as a laser. Only in the embodiment where the light guide has two reflectors (FIGS. 4A and 4B), the light is redirected 912 by an additional reflector. The light is subsequently reflected 914 by the additional reflector (or reflector in the embodiment with only one reflector— FIGS. 2A and 2B) orthogonally through the transparent surface into the cavity.

A signal is then detected 916 by a detector. The intensity of the electric signal depends on the amount of fluorescent marker present in the detection zone and the amount of light exciting it. The electropherogram plot of detector response with time may be generated from the detected signal.

The foregoing descriptions of specific embodiments of the present invention are presented for purposes of illustration and description. They are not intended to be exhaustive or to limit the invention to the precise forms disclosed, obviously many modifications and variations are possible in view of the above teachings. For example, the use of the word orthogonal should not be taken literally, but rather as approximately orthogonal. The embodiments were chosen and described in order to best explain the principles of the invention and its practical applications, to thereby enable others skilled in the art to best utilize the invention and various embodiments with various modifications as are suited to the particular use contemplated. Furthermore, the order of steps in the method are not necessarily intended to occur in the sequence laid out. It is intended that the scope of the invention be defined by the following claims and their equivalents.

What is claimed is:

1. A detection cell comprising: a substrate defining a cavity having a substantially planar floor and at least one wall with an opening therethrough, wherein said wall is not substantially optically flat; and a prism disposed adjacent said opening, where said prism is configured to redirect light through said opening into said cavity in a direction substantially parallel to said floor while avoiding said wall.

2. The detection cell of claim 1, wherein said detection cell forms part of an electrophoresis system.

3. The detection cell of claim 1, wherein said prism is selected from the group consisting of a right angled prism, a porro prism, a rhomboidal prism, a circular cylindrical prism, an elliptical cylindrical prism, a prism having a polygonally shaped cross-section, and combinations thereof.

4. The detection cell of claim 1, wherein said prism comprises: a transparent exit surface disposed adjacent said opening; and a reflector inclined at an acute angle to said transparent surface, where said reflector is configured to redirect light substantially orthogonally through said transparent surface into said cavity.

5. The detection cell of claim 4, where said transparent exit surface forms a boundary on one side of said opening.

6. The detection cell of claim 4, wherein said prism further comprises a transparent entry surface disposed substantially perpendicular to said exit surface.

7. The detection cell of claim 4, further comprising a shaft in said substrate adjacent said opening, where said shaft is substantially perpendicular to said floor, and wherein said prism is positioned at least partially within said shaft.

8. The detection cell of claim 4, further comprising an additional reflector disposed substantially parallel to said reflector, where said additional reflector is configured to redirect light toward said reflector.

9. The detection cell of claim 8, wherein said reflector and said additional reflector form opposing surfaces of said prism.

10. The detection cell of claim 8, wherein said reflector is mirrorized.

11. The detection cell of claim 8, wherein said additional reflector is mirrorized.

12. The detection cell of claim 4, wherein said transparent surface is substantially perpendicular to said floor surface of said cavity.

13. The detection cell of claim 1, further comprising: an additional wall defined by said cavity, where said additional wall defines a orifice therethrough opposing said opening; and an additional prism disposed adjacent said orifice, where said additional prism is configured to redirect light exiting through said orifice away from said cavity.

14. The detection cell of claim 13, wherein said additional prism comprises: a transparent exit surface disposed adjacent said orifice; and a reflector inclined at an acute angle to said transparent exit surface, where said reflector is configured to redirect light away from said cavity at an angle substantially perpendicular to said floor.

15. The detection cell of claim 1, further comprising an exit channel diametrically opposing said opening to divert potential scatter from said light away from said cavity.

16. A method for illuminating a chemical sample, comprising: directing light at a prism disposed adjacent an opening of a cavity containing a chemical sample therein; avoiding a wall of the cavity, wherein said wall is not substantially optically flat; and reflecting said light within said prism to pass through said opening and into said cavity to illuminate said chemical sample.

17. The method for illuminating a chemical sample of claim 16, further comprising, prior to said directing step, the step of positioning a chemical sample in said cavity.

18. The method for illuminating a chemical sample of claim 16, wherein said reflecting further comprises redirecting said light, at a reflector of said prism, toward said opening.

19. The method for illuminating a chemical sample of claim 16, wherein said reflecting further comprises redirecting said light, at an additional reflector, toward said reflector.

20. The method for illuminating a chemical sample of claim 16, further comprising, prior to said directing step, the steps of: boring a hole adjacent said opening; and positioning said prism in said shaft.

21. The method for illuminating a chemical sample of claim 16, further comprising subsequently reflecting said light away from said cavity by means of an additional prism.

* * * * *